United States Patent
Wiget et al.

[19]

[11] Patent Number: 5,920,167
[45] Date of Patent: Jul. 6, 1999

[54] ULTRASOUND DETECTION DEVICE IN PARTICULAR FOR AN AUTOMATICALLY CONTROLLED WINDSCREEN CLEANING SYSTEM

[75] Inventors: Fridolin Wiget, Neuchâtel; Eric Saurer, Bevaix, both of Switzerland

[73] Assignee: Asulab, S.A., Bienne, Switzerland

[21] Appl. No.: 08/993,440

[22] Filed: Dec. 18, 1997

[30] Foreign Application Priority Data

Dec. 19, 1996 [CH] Switzerland .............................. 3115/96

[51] Int. Cl.⁶ ............................................ B60S 1/08
[52] U.S. Cl. ..................... 318/444; 318/483; 318/DIG. 2
[58] Field of Search ................... 318/443, 444, 318/483, DIG. 2; 15/250.001, 250.12, 250.16, 250.17

[56] References Cited

U.S. PATENT DOCUMENTS

| | | |
|---|---|---|
| 4,180,886 | 1/1980 | Scherz . |
| 4,768,256 | 9/1988 | Motoda . |
| 5,266,873 | 11/1993 | Arditi et al. . |
| 5,432,415 | 7/1995 | Ittah et al. .............................. 318/483 |

FOREIGN PATENT DOCUMENTS

| | | |
|---|---|---|
| 0 626 593 A1 | 11/1994 | European Pat. Off. . |
| 0 631 146 A1 | 12/1994 | European Pat. Off. . |
| 2 692 535 | 12/1993 | France . |

*Primary Examiner*—Bentsu Ro
*Attorney, Agent, or Firm*—Richard K. Robinson

[57] ABSTRACT

A detection device has a transducer (10) for emitting and receiving series of ultrasonic pulses. An integrator (23) integrates echo signals resulting from ultrasonic pulses within a time window so as to produce an integral value. A time-delay circuit (28) is used to control the instant of opening T1 of a time window and a control circuit (25) determines an average value of a number of n integral values and for loading the values of the opening a instant T1 into the time-delay circuit (28) so as to maintain the average value at a steady value. The control circuit (25) determines the average value by loading a first value of T1 in the time-delay circuit before the integration of the first x echo signal and a second value of T1 in the time-delay circuit before the integration of the second n-x echo signals.

6 Claims, 4 Drawing Sheets

ULTRASOUND DETECTION DEVICE IN PARTICULAR FOR AN AUTOMATICALLY CONTROLLED WINDSCREEN CLEANING SYSTEM

The present invention concerns an ultrasonic detection devices and in particular an ultrasonic detection device for detecting the presence of foreign bodies such as water on a window. Such an ultrasonic detection device is intended for use with for example an automatically controlled windscreen cleaning system for a vehicle, and the invention will be described hereafter in relation with such an application. However, it should be understood that the invention is not limited to this application.

During the last few years, several devices of the type have been proposed for the automatically controlled cleaning of a window functioning with the ultrasonic detection of water on a surface.

Such a device, as described in the document EP-A-0 626 593, is attached to the interior surface of a windscreen of a vehicle and comprises a transducer which emits an ultrasonic pulse. The ultrasonic pulse propagates through the thickness of the windscreen and undergoes many internal reflections at the interface between the interior and exterior of the windscreen. The amplitude of these reflections diminishes with a rate which depends on the presence or the absence of water on the windscreen.

The electronic means associated with the transducer receive and process the resulting reflected echo signals. In fact, these electronic means measure the integral or the surface of the envelope of the echo signal within a time window which opens several tens of microseconds after the excitation pulse. This integral has a given value in the absence of rain and this value diminishes substantially with the presence of water on the windscreen. Thus, it is possible, by analysing the value of this integral to determine if there is water on the exterior surface of the windscreen and thus active the windscreen wipers.

However, it has been observed that in practice this way of approaching the problem has inconveniences. A problem associated with this device is that it possesses a limited resolution so that sometimes an unwanted functioning of the windscreen wipers is provoked.

The object of the present invention is to obtain an improved ultrasonic detection device which overcomes the inconveniences of the prior art.

The present invention has as its object an ultrasonic detection device arranged to detect a presence of foreign bodies, such as water, on a window, such as the windscreen of a vehicle, comprising a transducer for emitting a sequence of ultrasonic pulses which propagate through the thickness of said window and for receiving a series of reflected pulses resulting from each of said ultrasonic pulses, said transducer producing an echo signal representative of each of said series of reflected pulses, an integrator for integrating each of said echo signals within a time window so as to produce an integral value, a time delay circuit for controlling the instance of opening $T_1$ and/or of closing $T_2$ said time window, and a control circuit arranged, on the one hand, to determine an average value of a number of n integrated values and, on the other hand, to load a value of said instance of opening $T_1$ and or of closing $T_2$ into said time delay circuit so as to maintain said average value at a steady value, characterised in that said control circuit is arranged to determine said average value by initially loading a first value of $T_1$ and/or of $T_2$ in said time delay circuit before the integration of a first x of echo signals and secondly loading a second value of $T_1$ and/or of $T_2$ in said time delay circuit before the integration of a second n-x of said echo signals.

The description which follows indicates in more detail several features of the present invention. To facilitate the comprehension of the present invention, reference will be made to the annexed drawings in which the ultrasonic detection device is illustrated in an appropriate embodiment, and in which.

Figure 1:
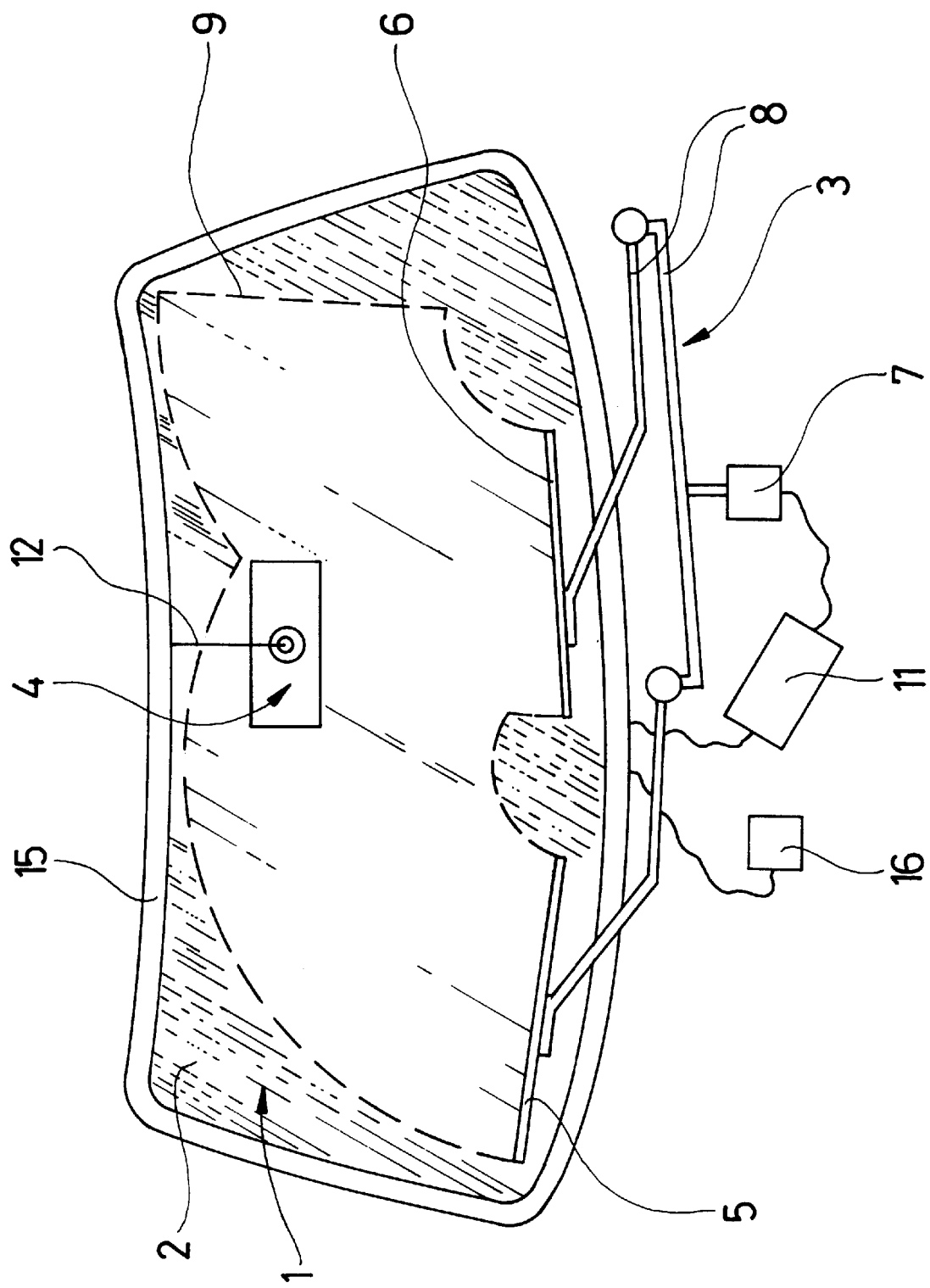
FIG. 1 is a schematic partial top view of a car windscreen equipped with an automatically controlled cleaning system having an ultrasonic detection device according to the present invention.

Reference will now first be made to FIG. 1, which shows a schematic view of windscreen 1 of an automotive vehicle equipped with an automatically controlled cleaning system having an ultrasonic detection device according to the present invention. The cleaning system is arranged to remove foreign bodies deposited on the exterior surface 2 of windscreen 1. In this example, the expression foreign bodies indicates elements such as water, snow, mud, etc, which may be deposited on the windscreen 1 and which may limit the visual range of the driver.

The cleaning system comprises a windscreen wiper-set 3 and an ultrasonic detection device 4 for detecting the presence of foreign bodies on the windscreen. The windscreen wiping-set 3 comprises, in a known manner, two wipers 5 and 6 driven by a motor 7 by way of a linkage 8. Wipers 5 and 6 are arranged to move along the exterior surface 2 of windscreen 1 according to an alternating movement in particular along an arc of a circle, and thus define a predetermined zone 9 delimited by dashed lines and representing the minimum visual range that the driver must have available.

Ultrasonic detection device 4 essentially comprises a transducer 10 and an electronic circuit 11 associated to this transducer. Transducer 10 is attached to the interior face of windscreen 1 and is electrically connected to circuit 11 by way of a coaxial cable 12 which passes along a gasket 15 of windscreen 1. A power supply circuit 16 formed for example by a battery of the vehicle is also connected to circuit 11.

Motor 7 which is connected to circuit 11 is used to activate wipers 5 and 6 when circuit 11 indicates the presence of water or another foreign body on the exterior surface 2 of the windscreen. Circuit 11 is, preferably, obtained in an integrated form so that it may be associated to transducer 10 in a single set.

Figure 2:
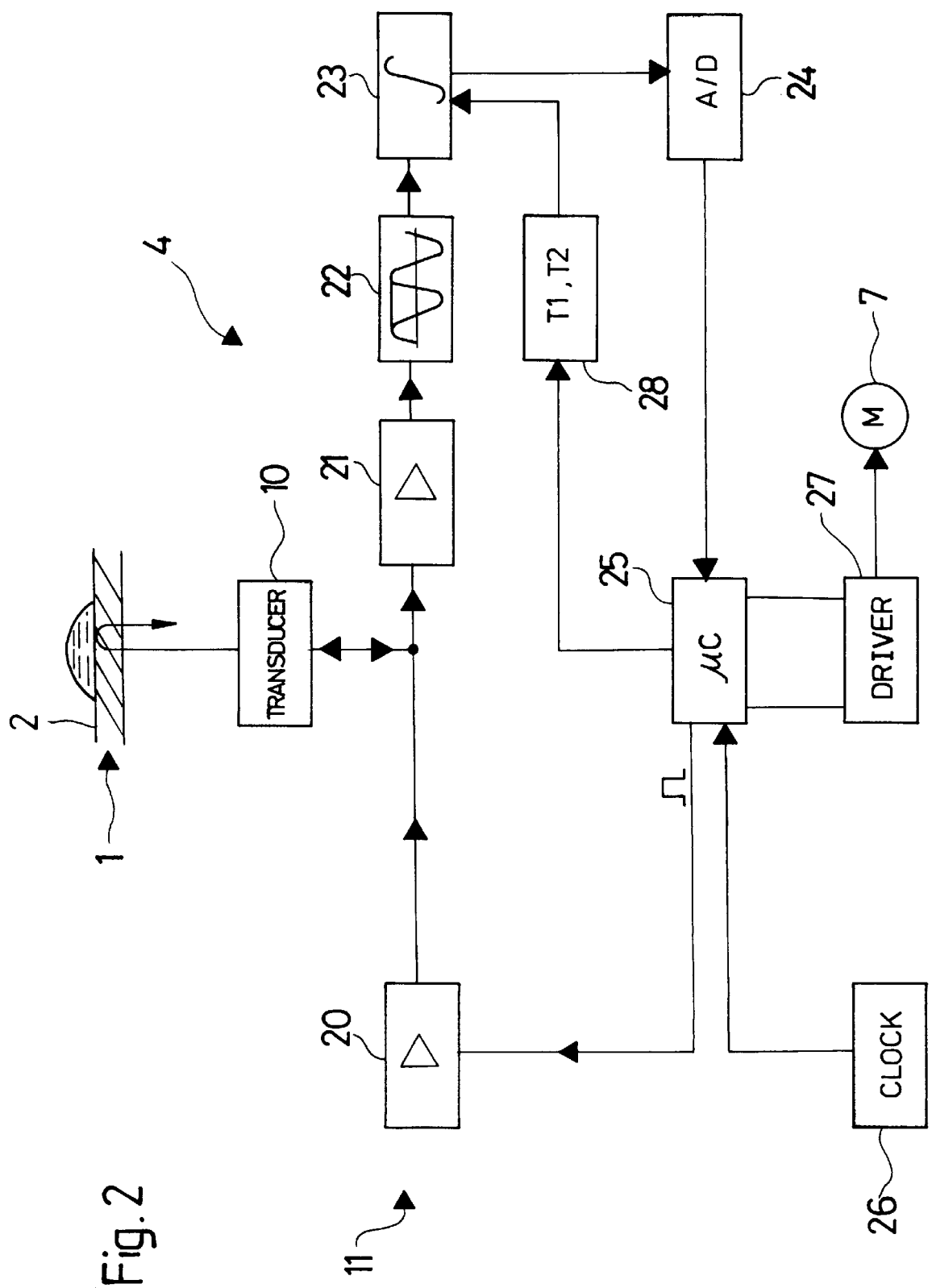
FIG. 2 is a block diagram of a realisation of an ultrasonic detection device according to the present invention.

FIG. 2 represents a block diagram of ultrasonic detection device 4 and of motor 7 of FIG. 1. Ultrasonic device 4 comprises ultrasonic transducer 10, two amplifiers 20 and 21, an envelope detector 22, an integrator 23, an analogue-digital converter 24, a control circuit 25, a clock circuit 26, a driving circuit 27, and a time-delay circuit 28.

Control circuit 25 generates pulses of a duration of 125 nanoseconds, at a frequency of 2.56 kHz determined by a clock circuit 26. These pulses are applied to the input of amplifier 20. The latter has a regulated gain so that the amplitude of the pulses at its output is around 10 volts. The pulses coming from the output of amplifier 20 are then applied to transducer 10.

The own-frequency of ultrasonic transducer 10 is around 4.5 MHz. Transducer 10 may be of any type and is used on the one hand, to emit a sequence of ultrasonic incident pulses, which each propagate through the thickness of windscreen 1, and on the other hand, to receive a series of reflected pulses resulting from the propagation of each emitted pulse.

Transducer 10 generates an electric echo signal following the reception of each series of reflected pulses. This echo signal is applied to the input of amplifier 21. Amplifier 21 transforms the echo signal of a peak voltage of 5 millivolts into a peak voltage of 500 millivolts.

The output of amplifier 21 is connected to envelope detector 22 which rectifies each echo signal by eliminating every alternating component, this filter increasing the precision of the integration which must be performed. Next, the envelope signal thus detected is applied to integrator 23, the latter being controlled by a time-delay circuit 28. Time-delay circuit 28 allows integrator 23 to integrate the envelope signal coming from envelope detector 22 during a predetermined time window. This time window may have a duration which is less than about 25 microseconds and it may be opened during an adjustable delay between 20 and 50 microseconds after that each pulse has been sent by transducer 10. The values $T_1$ and $T_2$, respectively corresponding to the instant at which this time window is opened and closed, are calculated and loaded into time-delay circuit 28 by control circuit 25.

After the closing of each time window, the analog-digital converter 24 converts the voltage at the output of integrator 23 into a digital value which is then transmitted to control circuit 25. Thus, the output of integrator 23 needs to be read only once every echo signal or, in this example with a frequency of 2.56 kHz. In order to reduce parasite values, the control circuit 25 stores a certain amount of consecutively measured digital values and calculates the average value of these values. In the embodiment shown by way of example in FIG. 2, the average of 256 consecutive values may be considered so that, with a repetition frequency between the ultrasonic incident pulses of 2.56 kHz, an average digital value is calculated at a rhythm of 10 per second.

Control circuit 25 adjusts the value of instants $T_1$ and $T_2$ and then loads these into time-delay circuit 28, on the basis of the digital values coming from analog-digital converter 27 so as to maintain the voltage at the output of integrator 23 at a steady state value. This steady state value, or simply steady value, preferably forms a substantial portion of the full scale input voltage of analog digital converter 24 so as to increase the resolution of ultrasonic detection device 4 to a maximum.

Figure 3:
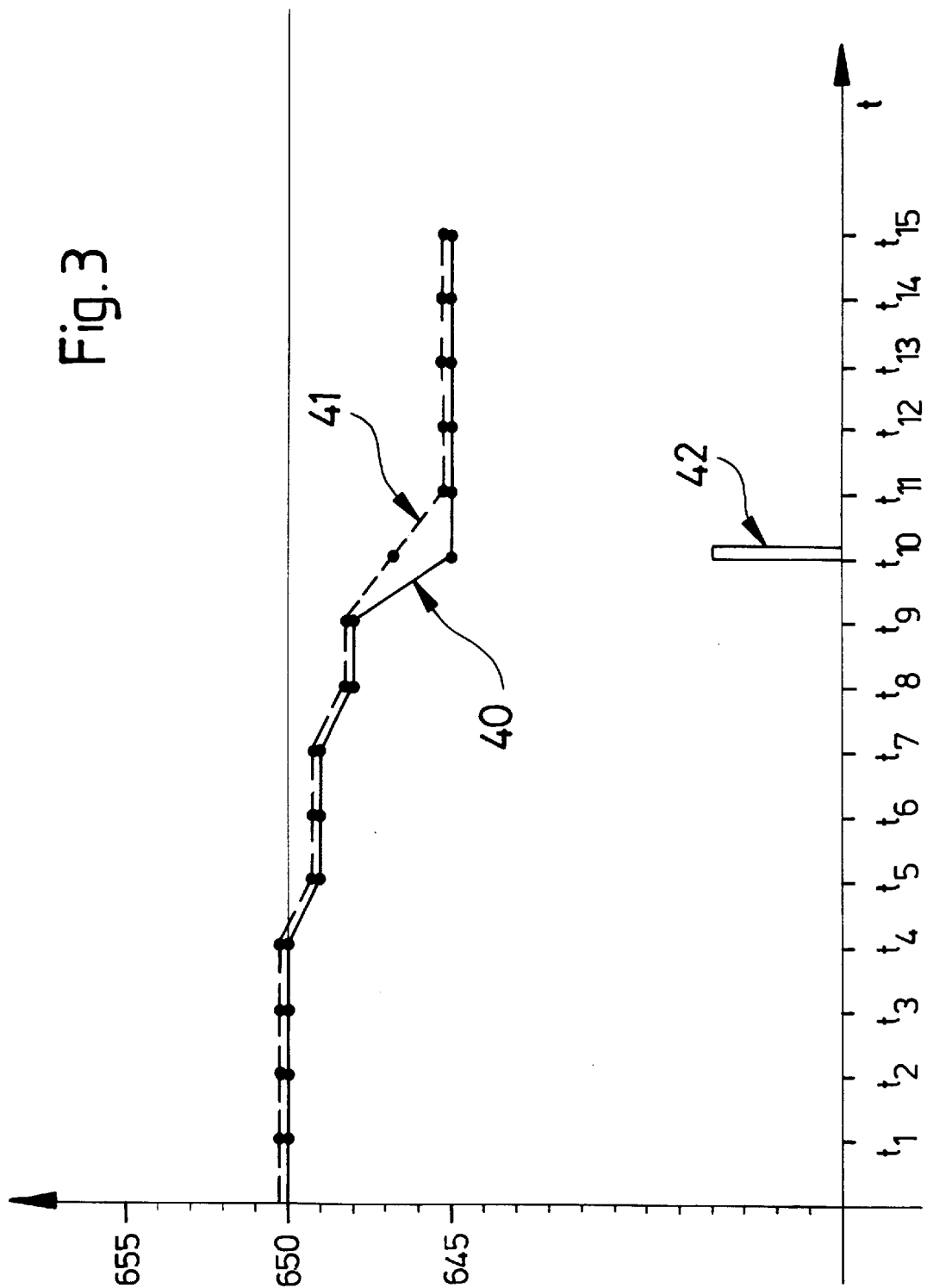
FIG. 3 is a graph which shows the time evolution of two calculated values by a control circuit forming part of the detection circuit of FIG. 2.

FIG. 3 shows a graphic representation of the average of 256 consecutive values of the output signal of analog-digital converter 24 (an average which is calculated by control circuit 25, as mentioned hereabove) symbolised by a continuous curve 40, and a reference value calculated by control circuit 25, symbolised by a dashed curve 41. As will be explained in more detail hereafter, a deviation of curve 41 of reference value 41 is used by the electronics to detect the presence of a foreign body on the windscreen and then to active motor 7 associated to the windscreen wipers.

Analog-digital converter 24 is adjusted such that the full scale input voltage corresponds to a digital value of $2^{10}-1=1,023$ (the connection between the analog-digital converter being in this example constituted by a 10-bit bus) and such that a zero input voltage corresponds to a digital value 0. The steady value of the average 40 of the measured integrals may thus correspond to a given numerical value, for example 650 units.

If there is no water or other foreign body present on the exterior surface 2 of windscreen 1 and if the ambient temperature is constant, the output signal of analog-digital converter 24 and the corresponding average digital values calculated by a control circuit 25, do not change. This is the case at instant $t_1$ and $t_4$ shown in FIG. 3. Therefore, control circuit 25 is arranged to calculate a reference value 41 slaved to an average value but with a limited variation rate. In other words, the reference value calculated by control circuit 25 follows that of average value 40 of the output signal of analog digital converter 24 in so far that the changing rate of the average value 40 is limited.

Experimentation has shown that the measured integral does not only depend on the presence of water and on the values of $T_1$ and $T_2$ but also, in a significant manner, on the temperature of the set windscreen-sensor. Thus, if the ambient temperature of windscreen 1 or if the functioning parameters of circuit 11 vary, the average value 40 may deviate temporarily from its steady value.

Such a situation is represented in FIG. 3 by the deviation at instants $t_5$ and $t_7$. Due to the thermic inertia of windscreen 1 and/or possibly due to the normal gradual deviation of the functioning parameters of circuit 11, these deviations are relatively slow. The deviation of the average consecutive digital values calculated by control circuit 25, with respect to the steady value of 650 units, may be, in this example, around 1 unit only between two measuring instants tn and $t_{n+1}$.

If such a deviation is detected by control circuit 25, the latter stops adjusting the values of $T_1$ and $T_2$ in the time-delay circuit 28 to maintain the output voltage of integrator 23 at a steady value. Control circuit 25 calculates a reference value 41 slaved to an average value but with a limited variation rate, in this case, to a unit change between two instants tn and $t_{n+1}$. Thus, the reference value calculated by the control circuit 25 follows that of average value 40 of the output signals of analog-digital converter 24, but with a maximum variation rate of only 1 unit between measuring instants $t_n$ and $t_{n+1}$. As long as consecutive average values 40 calculated by control circuit 25 do not have a variation of more than 1 unit, there is thus no deviation between the two curves 40 and 41, so that control circuit 25 does not generate a signal intended for the driving circuit 27 for operating motor 7. Thus, any activation of the windscreen wipers which is only due to temperature changes of the set windscreen-sensor is avoided.

However, if one or more drops of water fall onto the exterior surface 2 of the windscreen 1, an important attenuation of the amplitude is produced of the pulses of echo signals of transducer 10 and thus a fast drop of the average value 40, as illustrated by the deviation at instant $t_{10}$. In this case, control circuit 25 detects the deviation between the average value and the reference value.

Control circuit 25 sends an activation signal 42 to driving circuit 27 when such a deviation occurs between the two curves 40 and 41. In response to this signal, driving circuit 27 feeds motor 7 which then drives the two wipers 5 and 6 along the exterior surface of windscreen 1.

When the two curves 40 and 41 coincide again, control circuit 25 restarts to adjust the values $T_1$ and $T_2$ of the time window during which integrator 23 functions so as to reset the two curves to 650 units.

As is explained hereabove, the values of $T_1$ and $T_2$ are calculated by control circuit 25 before they are loaded into time-delay circuit 28. To facilitate the data processing which is necessary in the ultrasonic detection device 4, control circuit 25 and time-delay circuit 28 are realised as digital circuits such as an arrangement comprising a microprocessor and counters. Thus, the values of $T_1$ and $T_2$ are calculated and stored in a binary form. This implies that the values of $T_1$ and $T_2$ only have a limited resolution.

In the example described, the value of $T_1$ may vary from 30 and 50 microseconds with a resolution of about 0.25 microseconds. However, a jump of this size in the integral generated by integrator 23 may create a temporary deviation of several units of the average value 40 and, as a consequence, provoke an unwanted activation of the wipers. The variation of $T_1$ must thus be carried out with a much finer resolution.

To this effect, control circuit 25 modulates the value of $T_1$ during the period of acquisition and of calculation of the average of the mentioned 256 samples. In fact, control circuit 25 determines the average value by loading, firstly, a first value of $T_1$ and/or of $T_2$ into the time-delay circuit before the integration of the first echo signal and, secondly, the second value of $T_1$ and/or of $T_2$ into the time-delay circuit before the integration of the second echo signal.

Figure 4:
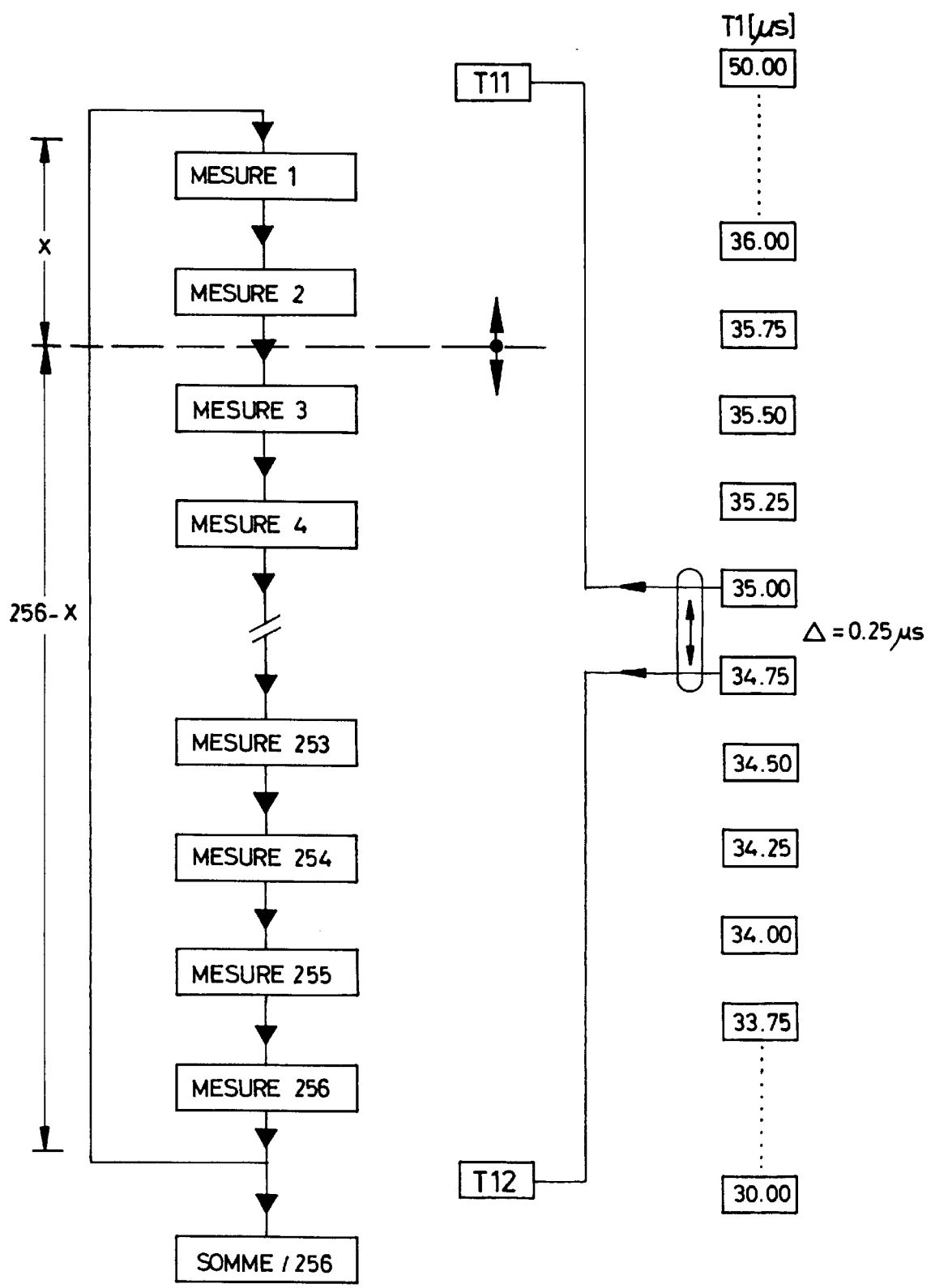
FIG 4 is a block diagram of a partial functioning algorithm of the control circuit of FIG. 3.

FIG. 4 shows how this modulation is obtained. This figure shows a range of possible values which may be taken on by $T_1$ in this example, i.e. 30.00 microseconds to 50.00 in steps of 0.25 microseconds. A representation of the measurement by control circuit 25 of the value of the integral is also shown, as seen at the output of the analog-digital converter 24, of each of the 256 samples (MEASURE 1, . . . , MEASURE 256), as well as the calculation of the average of these values (SUM/256).

Control circuit 25 is arranged on the one hand, to effectuate the first x measurements with a first value of $T_1$ loaded into time-delay circuit 28, for example 35.00 microseconds, and the last n-x measurements with a second value of $T_1$ loaded into time-delay circuit 28, for example 34.75 microseconds (in which n is equal to the number of samples i.e. 256 in this example and x is a variable which allows to modulate $T_1$).

It can thus be seen that the actual value of $T_1$ is $$\frac{(T_{11} \cdot x) + (T_{12} \cdot (n - x))}{n}$$

in which $T_{11}$ is the value of $T_1$ during the measurement of the first x samples and $T_{12}$ is the value of $T_1$ during the measurements of the other n-x samples. Consequently, the actual values of $T_1$ may now be selected per step of $$\frac{0.25 \mu \sec}{256} = 0.0009766$$

microseconds by varying the value of x in this case between 0 and 256. In the example described hereabove $T_{11}$ has a value of 34.00 microseconds, $T_{12}$ has a value of 34.75 microseconds, x has a value of 2 and n has a value of 256. In this case, the actual value of $T_1$ is 34.75195 microseconds.

Thus, a temporary deviation of several units of the average value 40 is avoided, and, consequently, an unwanted activation of the wipers is also avoided, by adjusting values $T_1$ and $T_2$.

The variation of x is cyclic. After several cycles have been carried out in the same direction, the values of $T_{11}$ and $T_{12}$ must be shifted by one step at the end of each cycle.

Preferably, the system comprises a $T_2$ having a fixed value. Only $T_1$ will be modulated in this case.

It should be understood that several modifications and/or additions may be carried out to the ultrasonic detection device according to the present invention without parting from the scope of the present invention which is defined by the annexed claims.

What is claimed is:

1. An ultrasonic detection device arranged to detect a presence of foreign bodies on a window, comprising:

a transducer for emitting a sequence of ultrasonic pulses which propagate through the thickness of said window and for receiving a series of reflected pulses resulting from each of said ultrasonic pulses, said transducer producing an echo signal representative of each of said series of reflected pulses;

an integrator for integrating each of said echo signals within a time window so as to produce an integral value;

a time delay circuit for controlling the instance of opening T1 and/or of closing T2 said time window, and a control circuit arranged, on the one hand, to determine an average value of a number of n integrated values and, on the other hand, to load a value of said instance of opening T1 and/or of closing T2 into said time delay circuit so as to maintain said average value at a steady value, wherein said control circuit is arranged to determine said average value by initially loading a first value of T1 and/or of T2 in said time delay circuit before the integration of a first x of echo signals, and secondly loading a second value of T1 and/or of T2 in said time delay circuit before the integration of a second n-x of said echo signals.

2. An ultrasonic detection device according to claim 1, further comprises cleaning averages for cleaning a predetermined zone of the exterior surface of said window, driving averages for driving said cleaning averages and for operating said cleaning averages in response to an indication of a foreign body on the exterior surface of the window.

3. An ultrasonic detection device according to claim 2, wherein said window is a windscreen, and in that said cleaning averages comprise a set of windscreen wipers for cleaning the exterior surface of said windscreen.

4. An ultrasonic detection device according to claim 1, wherein the control circuit is also arranged to calculate a reference value slaved to said average value but having a limited variation ratio, and averages for detecting temporary deviations between said average value and said reference value.

5. An ultrasonic detection device according to claim 4, further comprises cleaning averages for cleaning a predetermined zone of the exterior surface of said window, driving average for driving said cleaning averages and for operating said cleaning averages in response to an indication of a foreign body on the exterior surface of the window.

6. An ultrasonic detection device according to claim 5, wherein said window is a windscreen, and in that said cleaning averages comprise a set of windscreen wipers for cleaning the exterior surface of said windscreen.

* * * * *